United States Patent
Mucha (10) Patent No.: US 9,333,047 B2
(45) Date of Patent: May 10, 2016

(54) METHOD FOR GENERATING POSITION DATA OF AN INSTRUMENT

(75) Inventor: Dirk Mucha, Berlin (DE)

(73) Assignee: Flagon GmbH, Berlin (DE)

( * ) Notice: Subject to any disclaimer, the term of this patent is extended or adjusted under 35 U.S.C. 154(b) by 123 days.

(21) Appl. No.: 13/380,695

(22) PCT Filed: Jun. 25, 2010

(86) PCT No.: PCT/EP2010/003822
§ 371 (c)(1),
(2), (4) Date: Mar. 13, 2012

(87) PCT Pub. No.: WO2010/149371
PCT Pub. Date: Dec. 29, 2010

(65) Prior Publication Data
US 2012/0165655 A1 Jun. 28, 2012

(30) Foreign Application Priority Data
Jun. 26, 2009 (DE) .......................... 10 2009 030 731

(51) Int. Cl.
*A61B 5/05* (2006.01)
*A61B 19/00* (2006.01)

(52) U.S. Cl.
CPC ...... *A61B 19/5244* (2013.01); *A61B 2019/4894* (2013.01); *A61B 2019/5251* (2013.01); *A61B 2019/5272* (2013.01); *A61B 2019/547* (2013.01); *A61B 2019/5483* (2013.01)

(58) Field of Classification Search
CPC .......... A61B 17/2255; A61B 19/2203; A61B 19/5244; A61B 6/0457; A61B 6/102; A61B 6/4458; A61B 6/589; A61B 2019/4894; A61B 2019/5251; A61B 2019/5272; A61B 2019/547; A61B 2019/5483; B25J 13/088; B25J 9/1676

USPC ................... 600/426, 427, 429, 130
See application file for complete search history.

(56) References Cited

U.S. PATENT DOCUMENTS

2008/0121703 A1    5/2008    Li et al.

FOREIGN PATENT DOCUMENTS

| EP | 1380266 A1 | 1/2004 |
|---|---|---|
| WO | WO 9932033 A1 | 7/1999 |

(Continued)

OTHER PUBLICATIONS

Computer Assisted ENT Surgery, International Journal of Computer Assisted Radiology and Surgery; A Journal for Interdisciplinary Research, Development and Applications of Image Guided Diagnosis and Therapy, Springer, Berlin, DE, DOI 10.1007/s11548-006-0020-1, pp. 311 to 323.

(Continued)

*Primary Examiner* — Elmer Chao
(74) *Attorney, Agent, or Firm* — Davidson, Davidson & Kappel, LLC (57) ABSTRACT

A method for generating position data of an instrument (1), in particular a medical instrument, wherein the method includes the following steps: capturing position measurement data by way of at least one position sensor (7, 9) arranged on the instrument, determining a movement state of the instrument on the basis of the captured position measurement data, filtering the captured position measurement data on the basis of the determined movement state. A system for presenting an instrument, a computer program product including a program code, a computer program and a data storage medium including a program code.

25 Claims, 7 Drawing Sheets

(56) References Cited

FOREIGN PATENT DOCUMENTS

| WO | WO 2008110553 A2 | 9/2008 |
| WO | WO 2010054646 A2 | 5/2010 |

OTHER PUBLICATIONS

Mucha et al., "*Plausibility check for error compensation in electro-magnetic navigation in endoscopic sinus surgery*" in: International Journal of Computer Assisted Radiology and Surgery, Bd. 1, Nr. 7 (2006) 317-318.

METHOD FOR GENERATING POSITION DATA OF AN INSTRUMENT

The present invention relates to a method for generating position data of an instrument, in particular a medical instrument. Further, the present invention is directed to a system as well as a computer program product with a program code, a computer program and a storage medium with a program code for executing the method.

BACKGROUND

When working with an instrument in an area which is not clearly visible, it is of importance to detect or determine the current location of the instrument in order to be able to further process the detected location or position data in a suitable way. A known method is to furnish an instrument with electromagnetic position sensors and further to provide a field generator such that a control unit which is connected with the field generator and the position sensor(s) may detect position data of the instrument and display them on a display apparatus. From the essay "Plausibility check for error compensation in electromagnetic navigation in endoscopic sinus surgery" by Dirk Mucha et al., published as Proc. Computer Assisted Radiology and Surgery CARS, P. 3 17-18, 2006, it is known to furnish an instrument with two position sensors. For treating or handling a problem of field distortion by metallic devices, it is known to carry out a plausibility check of measured position measurement data. However, no method for additionally treating errors in the context of movements in a suitable way is known.

SUMMARY OF THE INVENTION

It is an object of the present invention is to provide a further method for generating position data of an instrument, in particular of a medical instrument.

The method encompasses the following steps: detecting position measurement data of at least one position sensor which is arranged on the instrument, determining a movement condition of the instrument based on the captured position measurement data, and screening or filtering the captured position measurement data based on the determined movement condition. Hereafter, at least the location of the instrument with regard to a certain coordinate system and/or at least one orientation of the instrument in this coordinate system are denoted as position of a tool. In particular field strength data of position sensors which are suitable for providing at least one position and/or at least one orientation of the position sensor and the instrument to which the sensor is attached are denoted hereafter as position measurement data. A position sensor may for example be embodied as electromagnetic sensor, for example as a coil or a set of coils, but other devices which are able to output location and/or position information are also possible. In other words, a method is provided by which the position of an instrument may be determined without the user of the instrument having to have a direct visual contact with the instrument.

In a preferred embodiment, the position of an instrument may be presented or displayed on a display apparatus, whereby the presentation of the instrument takes place based on at least screened or filtered position measurement data which were screened or filtered based on a movement condition.

An advantageous development of the present invention provides that the captured position measurement data are established based on at least one current position measurement. Thus, data which represent the current or present position of the instrument, for example in a control, are available and, for example, may be processed.

In a suitable embodiment of the present invention, it may be provided that the captured position measurement data encompasses a multitude of position measurements. This is enabled for example by a memory which is provided in a control apparatus which is configured or programmed to carry out the method according to the present invention. The multitude of position measurements may, e.g., have been recorded under constant time intervals so that a test series of position measurements is available.

An advantageous embodiment of the present invention provides that a plausibility value is created on the basis of position measurement data which are determined using at least two position sensor which are arranged on the instrument.

Each of the position sensors which are arranged on the instrument may be configured to output position measurement data from which a position of the instrument may be determined.

For example, by means of suitable transformations, in particular an operating point of the instrument can be determined. Ideally, the evaluations of the position measurement data of all position sensors arranged on the instrument lead to the same operation point of the instrument. However, if a conductive, for example a metallic object is nearby one of the position sensors, the field structure in the proximity of this position sensor is changed such that a different operating point of the instrument is determined when evaluating the position measurement data of this position sensor than when evaluating the position measurement data of the mostly undisturbed position sensor. The magnitude or amount of the distance between the two determined operating point of the instrument is denoted as plausibility value. Thus, a large plausibility value means a large deviation of the determined operating points of the instrument. An error caused this way is denoted as external interference.

In a further preferred embodiment of the method according to the present invention, the image data set is an image data set from at least one method of the group which encompasses: computer tomography, digital volume tomography, magnetic resonance tomography, sonography, duplex examination, angiography, nuclear medical imaging, medical imaging methods encompassing the administration of contrast agents, fluoroscopy and radiological addition or subtraction methods.

In an advantageous embodiment of the present invention, it may be provided that the movement state is determined based on both currently detected and previously captured position measurement data. Different movements of the instrument such as for example translations or rotations or combinations of these movements with high or low speed may be evaluated and categorized this way and finally allocated or linked to a movement state.

In a suitable embodiment of the present invention, it may be provided that a plausibility threshold value is allocated or linked to each movement state. This way, it is possible with different or other values to define a plausibility threshold value based on past movements of the instrument for a further evaluation.

Preferably, a development of the present invention provides that filtering the captured position measurement data takes place based on at least one comparison of the plausibility value with the plausibility threshold value. As the plausibility value of a field distortion is influenced by a conductive, for example a metallic, body in the proximity of one of the position sensors, and since the plausibility threshold value is determined based on movement state of the instrument, a movement of the instrument is considered in a distorted field so that these different error sources can eventually be included into the position calculation. Herefrom, an presentation of the instrument on the display apparatus may result.

Preferably, a development of the present invention provides that filtering encompasses accepting the current position measurement data for the case that the plausibility value is smaller than or equal to the plausibility threshold value, and dismissing the current position measurement data for the case that the plausibility value is greater than the plausibility threshold value. Thus, if a plausibility value is greater than a plausibility threshold value, the corresponding current position is dismissed. This way, position value changes that are confusing for a user are prevented.

In a suitable embodiment of the present invention, it may be provided that the image data set is created based on at least current position measurement data and the plausibility value. The operating point of the instrument is preferably determined on the basis of the current position measurement data, and the plausibility value for example may be evaluated as the radius of a sphere which is formed around the operating point of the instrument as its center. This way, an uncertainty of the current operating point of the instrument can be considered for a downstream method or for a subsequent calculation (e.g., an alarm may be output). In a corresponding embodiment, the uncertainty of the operating point of the instrument may alternatively or additionally be communicated and/or visualized to the user, for example to the surgeon.

In a suitable embodiment of the present invention, it may be provided that based on the plausibility value and the captured position measurement data it is determined whether a self-interference and/or an external interference of the captured position measurement data exists.

Preferably, a development of the present invention provides that the external interference is determined on the basis of the plausibility value, and the self-interference is determined on the basis of the captured position measurement data. As an external interference, in particular an interference is considered or understood which by means of a conductive, for example metallic object, leads to position measurement data sets of the position sensors on the basis of which deviating operating points of the instrument are determined. As an self-interference, a movement, for example a positioning, of the instrument is considered. This means that the measured position of the instrument is not influenced or is influenced by insufficient calibration data. A self-interference may also be a rotation of the instrument. This means that the measured position of the instrument is influenced by the rotational movement. A self-interference may further encompass a movement of the instrument. This means that the measured position of the instrument is influenced by the translational movement.

According to a further aspect of the present invention, a system to determine the position data of an instrument, in particular of a medical instrument, and/or to present an instrument or sections hereof on a display apparatus is provided, wherein the system encompasses: At least one position sensor arranged on the instrument for capturing position measurement data of the instrument and a data processing device which is configured to execute the method according to the present invention. In a preferred embodiment according to the present invention hereof, the system is suitable and configured to present an image data set which was determined on the basis of the previously described method. In an again preferred embodiment according to the present invention, the system comprises an operating system. The operating system is preferably a Unix operating system such as for example Solaris, UnixWare or IRIX, or a Unix derivative or BSD operating system such as for example Linux, NetWare, GNU/Hurd, FreeBSD, or NetBSD. The operating system is further preferably an operating system which is executable on an Apple or Apple/Macintosh computer such as for example Mac OS or Mac OS X. The operating system may furthermore preferably be a product of Microsoft, for example Windows in each type or version which is known to the person skilled in the art, for example Windows XP, Windows Me, Windows 2000, Windows Vista, Windows 7, Windows CE, Windows NT, and so on.

In a further preferred embodiment, image data are allocated to anatomical characteristics or to the morphology. This may take place for example by means of surface-based or interface-based registration processes or a pair of points registration.

Another aspect of the present invention provides a computer program product with a program code which is configured to execute the described method when the program code is executed on a computer. Another aspect of the present invention relates to a computer program which encompasses instructions that are configured to execute the described method when the computer program is run on a computer.

The program code is preferably present in the programming language C, C++, C#, Java, Delphi, Ada, Fortran, Cobol or in an interpreter or script language such as JavaScript, Python, Perl, Python, Lua, Ruby or Matlab Script.

According to a further aspect, a data storage medium with program code is provided which is configured to execute the described method when the program code is run on a computer.

The method according to the present invention as well as the system, the computer program product and the computer program and the data storage medium with the program code enable a user of an instrument in the above described way to gain profound knowledge of the position data and, if desired, also a secure instrument guidance, even if he has no visual contact with the instrument. The instrument may for example be a pointer, driller, guide wire, catheter, endoscope, biopsy needle, cutting instrument or any other instrument, in particular of the medical field.

Independent of the above-described method, system, computer program product, computer program and data storage medium, an endoscopy system is provided which encompasses at least one navigation module and a monitor, which is configured to provide at least one synchronized video and navigation information on the monitor, in particular an endoscopy monitor. Preferably, the endoscopy system is configured to present video and navigation information which was synchronized based on the above-described method on the monitor. The synchronization encompasses for example an update of the sphere which is formed around the operating point of the instrument and determined on the basis of the plausibility value and the captured position measurement data, as described above, for illustrating a measurement uncertainty. Updating the presentation may for example be based on an update of the image data set which is each displayed.

BRIEF DESCRIPTION OF THE DRAWINGS

In the following, the present invention is clarified by means of preferred embodiments with reference to figures of a drawing. Here, the figures show.

DETAILED DESCRIPTION

Figure 1:
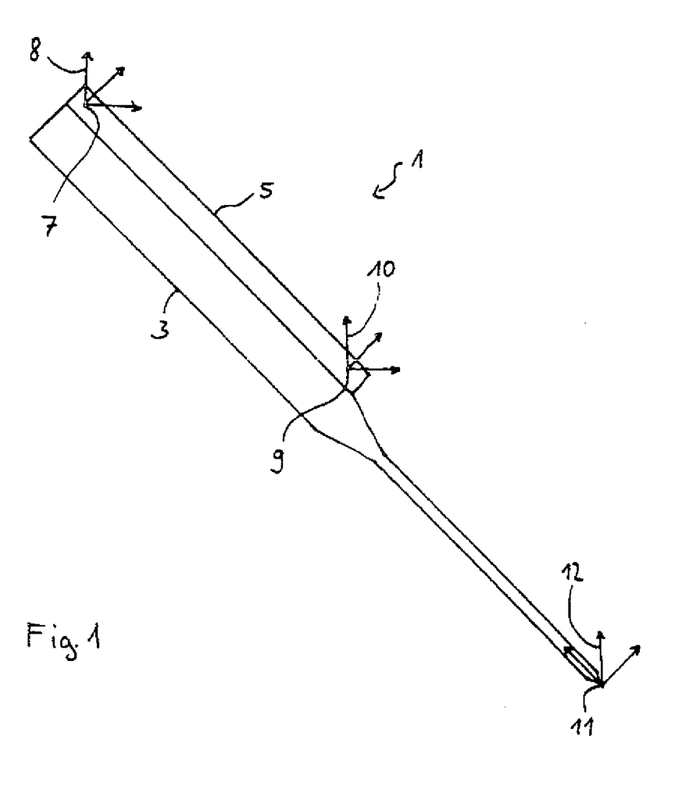
FIG. 1 shows in a schematical illustration an instrument with two position sensors and coordinate systems.

FIG. 1 shows an instrument 1, in particular a medical instrument 1 at which a locator 5 is firmly arranged, at which two position sensors 7 and 9 are installed. The instrument 3 is in this example furnished with a tip 11 which illustrates the operating point of the instrument. Local coordinate systems are allocated to the relevant points: A coordinate system 8 with origin 7 is allocated to the position sensor 7, a coordinate system 10 with origin 9 is allocated to the position sensor 9 and a coordinate system 12 with origin 11 is allocated to the operating point 11 of the instrument. The position sensors 7 and 9 capture or detect an electromagnetic field which is generated by means of one or more field coils. The measurement values of the position sensors 7 and 9 are forwarded or sent to a control device (not shown here). The control device is configured to calculate a position of the local coordinate systems 8 and 10 from the position measurement data of the respective position sensor 7 and 9. Here, 'position' means in particular the location in a three-dimensional coordinate system as well as the orientation of the respective position sensor 7 or 9. In the ideal case, the position of the operating point 11 of the instrument, i.e. origin and orientation of the coordinate system 12 may be calculated already from the position indications or information of one single position sensor based on the known geometry of the instrument 3.

Figure 2:
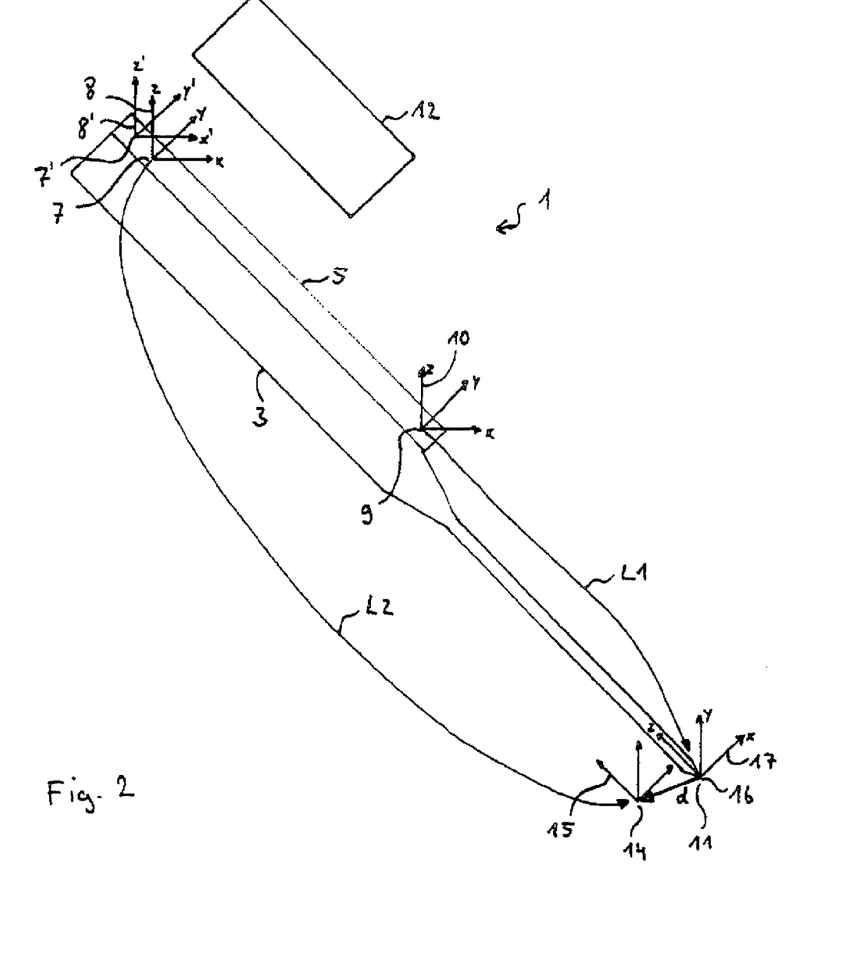
FIG. 2 shows an instrument as in FIG. 1 with a baffle block or an impediment.

FIG. 2 shows the instrument of FIG. 1, wherein same reference numerals refer to same components. In the case illustrated in FIG. 2, an interfering object 12 is situated in the proximity of the instrument 3. The object 12 is interfering in a way that it is in a position to change the fields generated by means of the not shown field coil or field coils such that the signals read from the position sensors 7 and 9 are evaluated in an undesired way. This effects that the evaluation of the position measurement data of the position sensor 9 which has a great distance from the interfering object 12 determines a coordinate system 17 with an origin 16 in the control unit as a result for the position of the operating point of the instrument, while the evaluation of the position measurement data of the position sensor 7 provides a coordinate system 15 with an origin 14 as result. The deviation between the origins 16 and 14 of the coordinate systems 17 and 15 is designated as d. The absolute value of this vector d is designated as plausibility value and is hereafter further used. The control unit of the evaluation unit has no information about which of the position sensors is interfered more. Thus, the control unit is not able to decide which of the coordinate systems 15 with origin 14 or 17 with origin 16 presents the operating point of the instrument better. For presentation on a display apparatus, the instrument tip is thus furnished with a circle of a sphere, the diameter of which corresponds to the plausibility value so that a user of suchlike system is able to decide on the basis of this monitor presentation how precisely or less precisely the instrument is arranged in this moment in the space. Another problem is that when the instrument is moved, i.e. a dynamic state is taking place, the plausibility value also increases due to the measuring rate of the system. This means that the movement is also registered as an interference, which is denoted as self-interference. As position measuring data which are contained with a too high plausibility value are not supplied to a visualization, a quick movement of the instrument may have the consequence that the navigation information for the moved instrument is not displayed. This is uncomfortable for the user. A increase in safety which is achieved by the plausibility check takes place at the expense of the availability of the navigation information. This loss has to be prevented in order to be able to utilize the system ergonomically.

As the interference may occur at an undefined or unknown point of time and with not a priori or previously known effect on the measured instrument position, the following is required from an error handling which minimizes the risk:

The interferences which currently influence the measurement of the instrument position according to static error correction, have to be identified and quantified by the system.

The error recognition examines in each measurement cycle the measuring values at runtime.

The error recognition shall not be supported by an optical or mechanical reference system because this way the system build-up becomes unergonomic and cost-intensive.

The recognized quantified interference shall sufficiently precisely correlate with the actually occurring position measurement error at the operating point of the instrument. Sufficiently precise means here that dynamic position measurement errors which are above a safety value of maximum 2 mm are recognized with a probability of 95%.

Measurement values which are impinged with a dynamic measurement error are further processed. Processing leads to the correction of the measurement values or the exclusion from navigation or presentation or display with a special labeling.

To meet these requirements, a concept is designed which is based on dynamic error recognition. This error recognition, which is hereafter denoted as plausibility check, is hereafter explained in more detail. The further components of the concept which are based on this are explained afterwards.

The gist or main idea hereby is to differentiate between a self-interference and an external interference, caused by another object, and to treat these interference classes differently. The class external interference is hereby treated as described above for reasons of risk minimization. This means that at least an error sphere around the operating point of the instrument is displayed. The class of self-interference is again subclassified into movement states. During use of the navigated instrument, different movement states occur. A precision requirement concerning the presented position is linked with each movement state.

Table 1 shows the defined state classes and table 2 qualitatively describes the requirements concerning the single movement states. From the precision requirement which is allocated to each movement state it results that interferences during dynamic processes such as moving the instrument in the operating area have to be treated less strictly. This means that the threshold value for the risk class may be higher in the moving state. This way, these self-interferences are not filtered out.

TABLE 1

| State | State description | Description of the measurement situation |
|---|---|---|
| z = 1 | external interference | The measured position of the instrument is influenced by another object |
| z = 2 | self-interference - positioning the instrument | The measured position of the instrument is not influenced or is influenced by insufficient calibration data |
| z = 3 | self-interference - rotation of the instrument | The measured position of the instrument is influenced by the rotational movement |
| z = 4 | self-interference - moving the instrument | The measured position of the instrument is influenced by the translational movement |

TABLE 2

| Movement state | Definition | Precision requirement |
|---|---|---|
| Positioning | The instrument is kept still in a position or moved or rotated with low speed. | High - The user compares in this state the current position of the instrument in the patient with the displayed position on the monitor. The information requires a low measurement uncertainty as distances to sensitive structures should possibly be illustrated and the instrument carries out an activity at this position (e.g., drilling). The instrument is not actively used. |
| Rotation | The instrument is swung or turned around its own axis. | Medium - The user aligns the instrument in order to achieve the movement state positioning. The instrument is not yet actively used in this state. |
| Moving | The instrument is moved with a speed of > 5 mm/s (translation). | Low - The user moves the instrument in the working area. By means of the presentation on the monitor, he receives a rough guide within the anatomy. Due to the movement, a precise visual comparison with the image data is not possible. In this movement state, the operation point is localized or identified. |

Thus, a method for generating image data for displaying an instrument, in particular a medical instrument, on a display apparatus is created, wherein the method encompasses the following steps: capturing position measurement data of at least one position sensor which is arranged at or on the instrument, determining a movement state of the instrument on the basis of the captured position measurement data, filtering the captured position measurement data on the basis of the determined movement state and providing an image data set for an amended presentation or display of the instrument at least on the basis of the filtered position measurement data which is configured to present the instrument.

Figure 3:
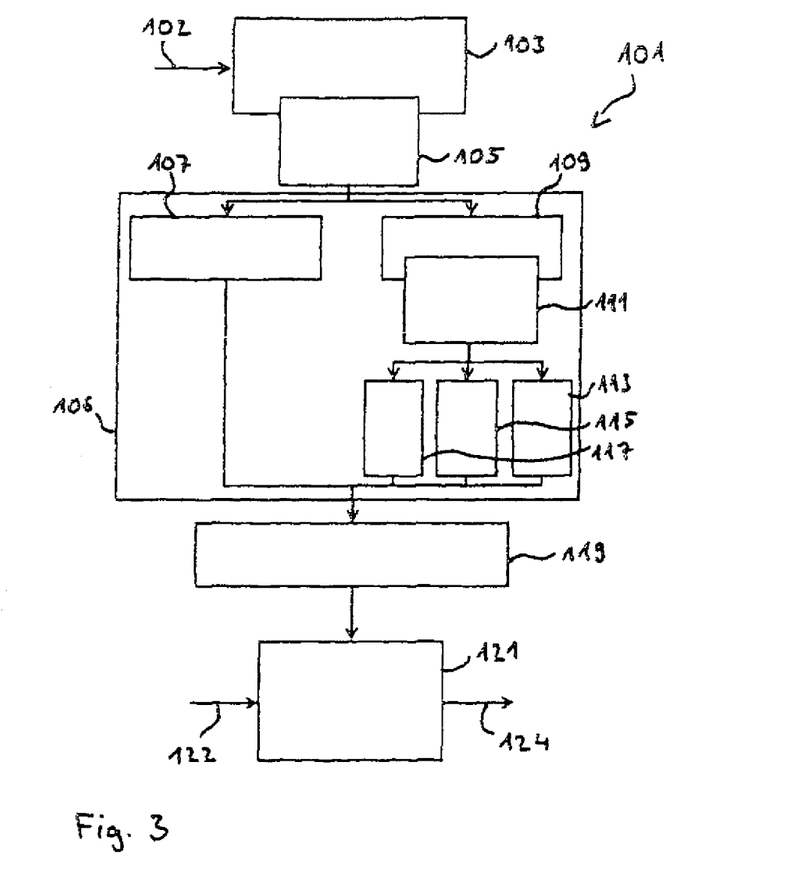
FIG. 3 shows a concept of adaptive threshold value filtering.

FIG. 3 illustrates a concept of the realization of an adaptive default threshold value. According to this, initially a latch 103 is provided which is required to store a signal pattern for a subsequent statistical analysis. Current measurement values, for example position or location data p(k) which are supplied to an input 102 as well as n previous measurement values are saved or stored. Furthermore, the current plausibility value d(k) is supplied to the input.

An interference classifier 105 concludes the type of interference from the saved or stored signals. A differentiation is made between external interference and self-interference. Interferences which are not identifiable or recognizable are also classified as self-interferences.

Thus, a separation or distinction between an external interference treatment 107 and a self-interference treatment 109 is already made at the input of a state determination 106.

If it was determined by the interference classifier 105 that there is a self-interference, a movement classifier 111 concludes the current movement state of the instrument from the signal. Herefor, the signal patterns for the single states were previously analyzed and criteria or classification were modeled or worked out, as will be shown further below. With the aid of these criteria, classification during runtime or on the run may take place. The movement states positioning 117, moving 115 and rotating 113 are defined. These states are explained in more detail in table 2.

The movement state as determined in the state determination 106 which describes the current measurement situation, is supplied to a threshold value parameterization s=f(z), 119. The threshold value parameterization s=f(z), 119, allocates a threshold value to each determined movement state, which is evaluated in a subsequent step. Suitable threshold values were previously or a priori experimentally determined. The threshold value which was determined by the threshold value parameterization 119 is supplied to the threshold value filter 121. The threshold value filter 121 compares the current plausibility value p(k) which was supplied via the input 122 with the parameterized threshold value s=f(z) for the risk class. Measurement values which fall under the risk class are filtered. The threshold value is continuously adapted to the current movement state.

The adaptive threshold value filter enables a displaying of the navigation information during higher dynamics of the instrument if no external interference is identified. At the same time, the safety concept is not violated.

Figure 4:
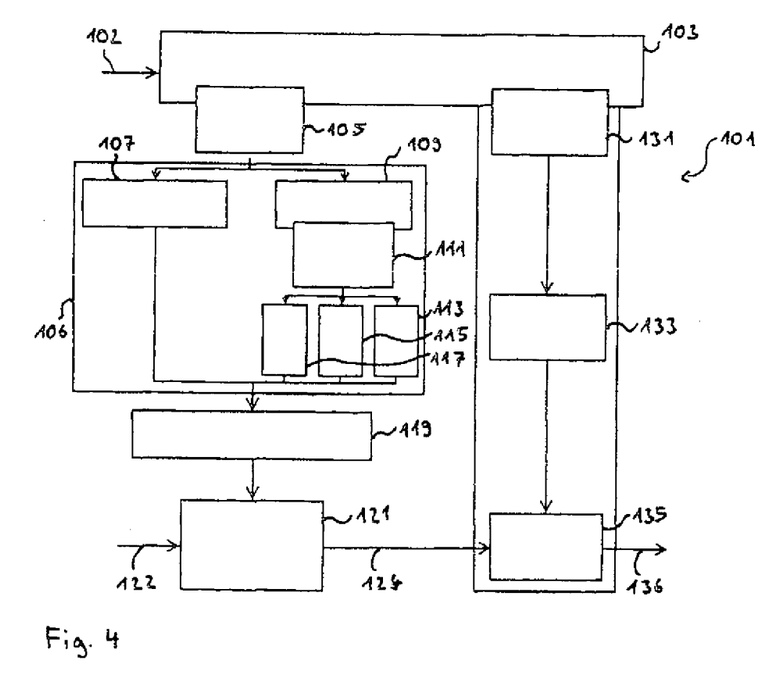
FIG. 4 shows a concept of adaptive threshold value filtering as in FIG. 3 with an add-on or extension.

FIG. 4 illustrates an extended filter concept. The treatment of dynamic errors as described above was aimed exclusively at filtering out, i.e. dismissing erroneous measurement values. With the signal conditioning, the filter concept shall again be extended by a component which corrects dynamic errors which were caused by self-interference. The filter 101' supplies a corrected measurement value p'(k) at the output 136 to each measurement value, i.e. to measured position or location data p(k) at the input 102. FIG. 4 illustrates the operation of the filter to be designed. The blocks 131, 133 and 135 are integrated into the existing filter design between the latch and the actual signal path. Preprocessing may take place in parallel to the classification of the threshold value filter. The component signal conditioning 135 which manipulates the position measurement data is arranged in the signal path 124 behind the threshold value filter 121. The data rate in the signal path is not changed by the filter concept. This means that processing of the signals can be carried out in one measurement cycle.

The added single function blocks of the extended filter are a data preparation 131 which uses the saved or stored signal data to generate further signals from them, for example speed, correlation and/or variance or deviation. In a model-to-model comparison 133, the signal patterns can be analyzed and compared with the specifications of a model. Parameters for the component of the signal conditioning 135 are deduced from this. The signal conditioning 135 manipulates the currently measured and filtered position measurement values p(k). The value p'(k) which is present at the output 136 is thus a function of p(k) and at least the determined movement state.

The movement classifier 111 evaluates the saved or stored signal patterns with regard to interference and movement state of the instrument. For this, suitable criteria for a classification were found previously and/or in an earlier examination. In the examination, signal patterns of the instrument operating point patterns depending on the different position sensor data were recorded. For this, a certain movement such as for example translation, rotation or positioning was each carried out. The signal patterns were analyzed with regard to distinct features. For signal analysis, three variables were introduced by means of which the signals can be characterized: At first, the correlation coefficient was introduced which describes the correlation between the two signals of the operating point of the instrument for the saved measurement values. Then, the memory variance was used which is a dimension for the divergence of the saved measurement values. Finally, an instant variance was used which is a dimension for the divergence of the last three measurement values. This signal follows quick changes faster than the memory variance. The variance was introduced because the variance is higher during a movement than with a stillstanding, i.e. positioned instrument. It was discovered that a translation is not present or is not taking place if one of the following criteria applies: criterion 1: the correlation coefficient of all degrees of freedom (x, y, z) are smaller than an experimentally determined value; criterion 2: the correlation coefficients of 2 degrees of freedom are negative; or criterion 3: the instant variances of all degrees of freedom are smaller than an experimentally found value. With regard to a rotation which describes a swinging movement of the instrument during which the operating point of the instrument remains in one position, it was discovered that there is no rotational movement if criterion 4 applies stating that the instant variances of all degrees of freedom are smaller than an experimentally determined value.

An interference state caused by a foreign object is present if one of the following criteria is met: criterion 5: The memory variances of all degrees of freedom are smaller than an experimentally determined value; or criterion 6: The correlation coefficients of exactly two degrees of freedom are smaller than an experimentally determined value and the remaining degree of freedom has a correlation coefficient which is smaller than a negative value which was determined experimentally.

The three variables correlation coefficient, instant variance and memory variance are calculated for each measurement cycle k by means of the movement classifier 111 from the latch for the degrees of freedom of both position measurements.

Figure 5:
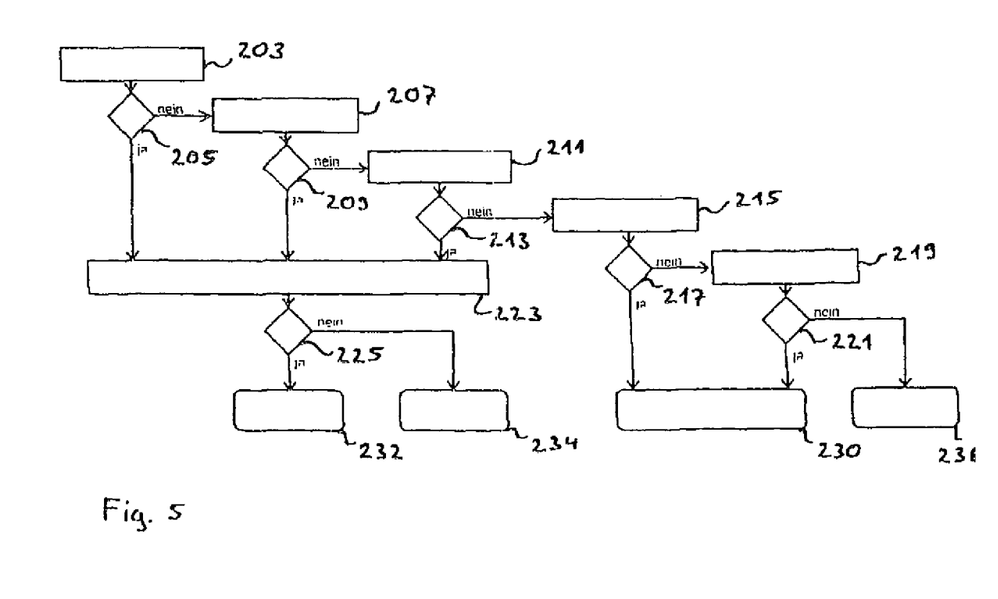
FIG. 5 shows a classification algorithm to determine a movement state of the instrument.

FIG. 5 illustrates an algorithm for classification, i.e. for determination of a movement state, on the basis of the above-defined criteria. In doing so, the criteria are successively checked and decisions are made. As an result, the algorithm provides for a movement state which is used for parameterization of the threshold value filter. Thus, the classification algorithm 201 which is illustrated in FIG. 5 checks the above-defined single criteria and finally determines a movement state of the instrument. In a step 203, the algorithm checks whether criterion 1 is met, and branches off in 205. In the case that criterion 1 is not met, the algorithm continues in 207. In the case that criterion 1 is met, the algorithm continues in 223. In 207, the algorithm checks criterion 2 and branches off in 209. In the case that criterion 2 is not met, the algorithm continues in 211. In the case that criterion 2 is met, the algorithm continues in 223. In 211, the algorithm checks criterion 3 and branches off in 213. In the case that criterion 3 is not met, the algorithm continues in 215. In the case that criterion 3 is met, the algorithm continues in 223. In 215, the algorithm checks criterion 5 and branches off in 219. In the case that criterion 5 is not met, the algorithm continues in 211. In the case that criterion 5 is met, the algorithm ends in 230 and determines the movement state as interference state, z=1. In 219, the algorithm checks criterion 6 and branches off in 221. In the case that criterion 6 is not met, the algorithm ends in 236 and has determined as a movement state the translation, z=4. In the case that criterion 6 is met, the algorithm ends in 230 and determines the movement state as interference state, z=1. In 223, the algorithm checks criterion 4 and branches off in 225. In the case that criterion 4 is not met, the algorithm ends in 234 and has determined the movement state as rotation, z=3. In the case that criterion 4 is met, the algorithm ends in 232 and has determined the movement state as positioning, z=2. A threshold value is allocated to each of the determined movement states, i.e. interference state, positioning, rotation and translation. As is illustrated in the FIGS. 3 and 4, a threshold value filter decides whether the current plausibility value d exceeds or falls below one of the parameterized threshold values. In the case that the determined threshold value is exceeded, the associated measurement value is dismissed, i.e. it is not output in 124 and thus is not available for a presentation of the instrument on the display apparatus. In the case that the plausibility values is smaller than the parameterized threshold value from 119, the current position value in 121 is allowed to pass to 124. The allocation of a movement state from the movement classifier to a threshold value is denoted as parameterization which is stored or maintained as a spreadsheet for each movement state. For preparing the spreadsheet, the single or particular threshold values were experimentally determined for the instrument. The last component in the signal path is the visualization of the position data, i.e. a presentation of the instrument on a display apparatus. The corrected and filtered data are transformed into an image data coordinate system and displayed. The visualization encompasses the following additional properties or features: 1. error estimation: The measurement uncertainty which is present due to the registration and the measurement interferences is estimated. As a measure for the registration uncertainty, a quality value from the registration algorithm is used. The value indicates the maximum deviation of the points which are registered to each other. As a simplification, this value is used direction-independently. The plausibility value d serves as a measure for erroneous position measurement values. It is calculated in each measurement cycle k. 2. Visualization of the measurement uncertainty: The estimated measurement uncertainty is visualized as a space around the illustrated position of the operating point of the instrument in the form of a sphere. In orthogonal sectional views, this is thus a circle. The dynamics of this display enables a user to judge the interference state of the current position measurement. 3. Visualization of the interference state: Measurement data which were dismissed by the threshold value filter are not used for the navigation display. This state of excessive interference is signaled to the user by red coloring of the instrument which is represented in the image data. The instrument is presented on the last valid measured position until a new valid measurement value is available.

Figure 6:
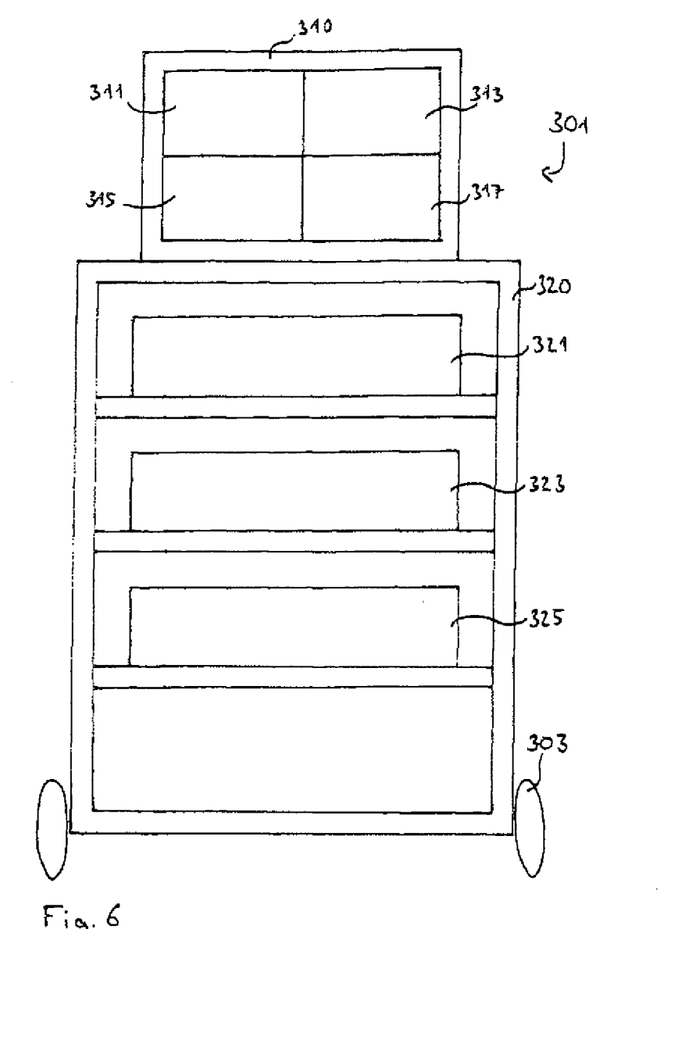
FIG. 6 shows a schematical structure of an endoscopy system with an endoscopy monitor and FIG. 7 shows an endoscopy monitor according to FIG. 6.

In FIG. 6, an endoscopy system 301 is exemplified which is provided independently of the above-described method, system, computer program product, computer program and data storage medium, but is able to effectively cooperate with the above-described method, system, computer program product, computer program and data storage medium. The endoscopy system 301 encompasses at least one monitor 310 and at least one navigation module 321 and is easily transportable by means of rollers or wheels 303. The endoscopy system 301 is configured to display at least one synchronized video and navigation information on the monitor, e.g. an endoscopy monitor. For example, the endoscopy system 301 is configured to present a video and navigation information on the monitor 310 which was synchronized on the basis of the above-described method. Synchronization encompasses for example an update of the sphere which is presented around the operating point of the instrument and determined on the basis of the plausibility value and the captured position data, as described above, to illustrate a measurement uncertainty. Updating the presentation may for example be based on an update of the respective displayed image data set. In an advantageous embodiment, it may be provided for a simultaneous visualization of several views to subdivide the monitor 310, during operation, in four partial views 311, 313, 315 and 317 by means of a suitable control of the monitor. The reference numerals 323 and 325 denote further standard modules which are provided on the endoscopy tower.

Figure 7:
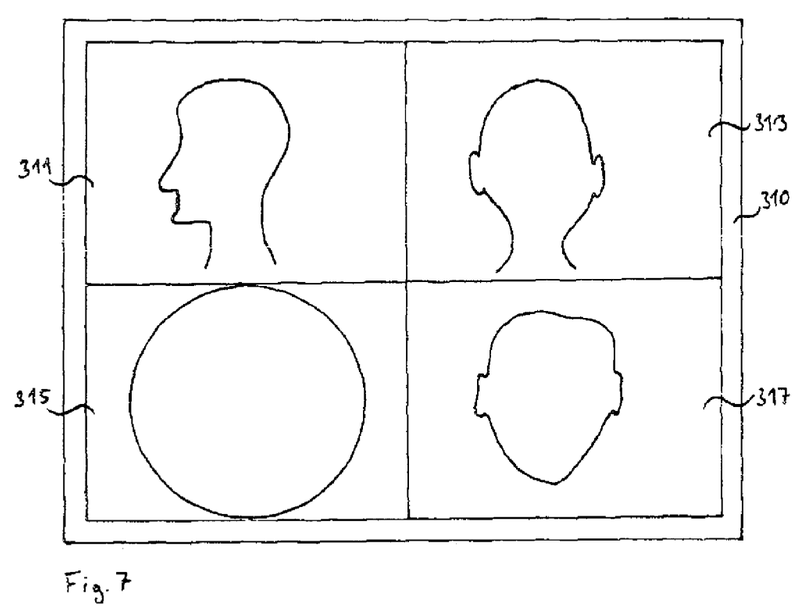

FIG. 7 illustrates an exemplary presentation of endoscopy information on an endoscopy monitor 310. The monitor 310 which was for example subdivided into four partial views by means of a suitable control of the monitor presents in a partial view 311 a sagittal section through a head of a patient, in a partial view 313 a coronary section, and in a partial view 317 an axial section through the head of the patient. In a partial view 315, e.g. synchronized video and/or navigation information can be presented. This information may for example have been calculated and/or processed according to the above-described method.

In other words, a documentation and treatment module for a navigation in the medical field is provided by means of the described endoscopy system 301.

The system to document and execute navigated interventions consists of at least one navigation module which may be provided as an additional component of a common video endoscopy tower. The system encompasses preferably at least one monitor. Preferably, this system is not configured as an additional mobile or stationary system but is integrated in the video endoscopy tower. The gathered video data may be recorded together with navigation data which are for example synchronized as described above for documentation purposes. Further, the module preferably encompasses interfaces for optical and/or magnetic navigation sensors. With this system, it is advantageously not necessary to make entries to the system during operation and/or during working with the system, Thus, a user is unburdened and can pay his or her attention completely to working in or on a surrounding of the operating point of the instrument. At least one electromagnetic navigation sensor can be mounted in a defined alignment at an operating table and be connected with the navigation module 321 such that the sensor data of the electromagnetic navigation sensor can be read and evaluated by the navigation module 321 and subsequently be presented on the monitor. At least one optical navigation sensor can be mounted to a self-retaining ball joint and be aligned with one hand by a user. The optical navigation sensor may be connected with the navigation module 321 such that the sensor data of the electromagnetic navigation sensor can be read and evaluated by the navigation module 321 and subsequently be presented on the monitor. Preferably, the system is configured such that the navigation information and the video information can be split between two monitors and displayed by them. For example, it may be provided that the navigation module communicates with the navigation sensor via a wireless connection. Suchlike connection could for example be furnished by means of a Bluetooth protocol. Furthermore, it may for example be provided that the navigation module obtains patient image data via a wireless connection. For example, access to a patient data base of a central server could take place via WLAN in a building.

The described system may in a suitable embodiment provide one or more of the following advantages: The navigation system may be provided as a module for an endoscopy tower so that handling is improved. The navigation system may be completely integrated in the modular endoscopy tower. Further, it may provide compatible interfaces to other, common endoscopy modules. A clinical workflow is significantly improved as no additional device is required. The optical navigation sensor which is for example embodied as a camera can be positioned separately from the endoscopy tower on a tripod. The camera interface is configured such that it supports all common navigation cameras. The navigation system is configured such that it can carry out video overlays, i.e. that different certain image data are presented for example on a monitor area in an overlayed way, so that a user is for example enabled to capture real image data and assessed and evaluated sensor data at the same time and with spatial allocation and thus carry out an improved navigation of the instrument during work. Finally, the described system is able to document the video data and sliced image data, i.e. for example furnish the data as momentary still image data or as data streams with a time stamp and save or store them.

The features of the present invention disclosed in the above description, the claims and the drawing may be of importance for realizing the present invention in its different embodiments both singularly and in arbitrary combination.

The invention claimed is:

1. A method for generating position data of a medical instrument, the method comprising the following steps:

capturing position measurement data of at least two electromagnetic position sensors which are arranged on the medical instrument, the position measurement data indicating a measured position of the medical instrument;

implementing by a data processor:

determining a movement state of the medical instrument on the basis of the captured position measurement data, the movement state being defined by how the medical instrument is being moved and a speed the medical instrument is being moved, the movement state being one of a positioning state in which the medical instrument is kept still in a position or moved or rotated with a speed lower than a predetermined value, a rotation state in which the medical instrument is swung around its own axis, a moving state in which the medical instrument is moved with a speed higher than a predetermined value, and an interference state in which the measured position of the medical instrument is influenced by another object, the determination comprising:

calculating variables describing a correlation between the position signals of the position sensors on the basis of the captured position measurement data, the calculated variables describing a correlation between the position signals of the position sensors are correlation coefficients for each degree of freedom of the medical instrument, calculating variables describing a dimension of the divergence of captured and previously measured position measurement data, the calculated variables describing a dimension of the divergence of captured and previously measured position measurement data are variances for each degrees of freedom of the medical instrument, determining the respective movement state of the medical instrument by means of an algorithm for classification comprising comparisons of the calculated variables with predetermined values where the algorithm for classification based on a decision tree comprising decision criteria to be checked, each decision criterium comparing the calculated variables to predefined values, depending on the result of a first decision criterium, at least one further decision criterium is checked and at the end of the decision tree a different threshold value is allocated to each of the determined movement states, and filtering the captured position measurement data on the basis of at least one comparison of the allocated threshold value with a predefined plausibility value to determine if the predefined plausibility value exceeds the allocated threshold value; and displaying an image data set based on the filtered captured position measurement data on a display, the image data set including a graphical depiction of the medical instrument, the graphical depiction being displayed on the display only when the predefined plausibility value does not exceed the allocated threshold value.

2. The method as recited in claim 1 further comprising:
allocating at least one coordinate transformation of the position sensor to at least one operating point of the medical instrument to each position sensor; and
determining the operating point of the medical instrument by mathematical combination of position measurement data of a position sensor and allocated coordinate transformation.

3. The method as recited in claim 1 wherein the image data set is at least one of an image data set of the group consisting of: computer tomography, digital volume tomography, magnetic resonance tomography, sonography, duplex examination, angiography, nuclear medical imaging, medical imaging by a contrast agent, fluoroscopy and radiological addition or subtraction.

4. The method as recited in claim 1 wherein the image data set is provided for an amended presentation of the medical instrument at least on the basis of the filtered position measurement data, which is configured to display the medical instrument.

5. The method as recited in claim 1 wherein the captured position measurement data is generated on the basis of at least one current position measurement.

6. The method as recited in claim 1 the captured position measurement data encompasses a multitude of position measurements.

7. The method as recited in claim 1 wherein the movement state is determined on the basis of currently captured position measurement data and position measurement data detected in the past.

8. The method as recited in claim 1 wherein criteria to differentiate movement states are logically combined.

9. The method as recited in claim 1 wherein the filtering encompasses accepting the current position measurement data for the case that the plausibility value is smaller than or equal to the plausibility threshold value, and dismissing the current position measurement data for the case that the plausibility value is greater than the plausibility threshold value.

10. The method as recited in claim 1 wherein it is determined on the basis of a logical combination of criteria whether a self-interference and/or an external interference of the captured position measurement data exists.

11. The method as recited in claim 1 wherein image data are allocated to anatomical characteristics or to a morphology by surface-based or interface-based registration methods or pair of points registration.

12. The method as recited in claim 1 wherein the determination of the respective movement state of the medical instrument and/or the algorithm for classification comprises checking at least two of the following criteria:

criterion 1: the correlation coefficient of all degrees of freedom are smaller than an experimentally predetermined value;
criterion 2: the correlation coefficients of two degrees of freedom are negative;
criterion 3: the variances of all degrees of freedom of the last three measurements are smaller than an experimentally predetermined value;
criterion 4: the variances of all degrees of freedom of the last three measurements are smaller than an experimentally predetermined value;
criterion 5: the variances of all degrees of freedom of the last measurements are smaller than an experimentally predetermined value;
criterion 6: the correlation coefficients of exactly two degrees of freedom are smaller than an experimentally predetermined value and the remaining degree of freedom has a correlation coefficient which is smaller than a negative experimentally predetermined value.

13. The method as recited in claim 12 wherein it is determined that the movement state is:
a positioning state when:
criteria 1 and 4 are met;
criterion 1 is not met but criteria 2 and 4 are met; or
criteria 1 and 2 are not met but criteria 3 and 4 are met;
a rotation state when:
criterion 1 is met and criterion 4 is not met;
criterion 1 is not met, criterion 2 is met and criterion 4 is not met; or
criteria 1 and 2 are not met, criterion 3 is met and criterion 4 is not met;
a moving state when:
criteria 1, 2, 3, 5 and 6 are not met; or
an interference state when:
criteria 1, 2, 3 are not met and criterion 5 is met; or
criteria 1, 2, 3 and 5 are not met and criterion 6 is met.

14. A system for displaying or presenting an instrument on a display apparatus, the system comprising:
at least two electromagnetic position sensors for capturing position measurement data of the medical instrument, the position sensors being arranged on the medical instrument, and
a data processor configured to execute a method for generating position data of the medical instrument, the method comprising the following steps:
capturing position measurement data of the at least two electromagnetic position sensors which are arranged on the medical instrument, the position measurement data indicating a measured position of the medical instrument;
determining a movement state of the medical instrument on the basis of the captured position measurement data, the movement state being defined by how the medical instrument is being moved and a speed the medical instrument is being moved, the movement state being one of a positioning state in which the medical instrument is kept still in a position or moved or rotated with a speed lower than a predetermined value, a rotation state in which the medical instrument is swung around its own axis, a moving state in which the medical instrument is moved with a speed higher than a predetermined value, and an interference state in which the measured position of the medical instrument is influenced by another object, the determination comprising:

calculating variables describing a correlation between the position signals of the at least two electromagnetic position sensors on the basis of the captured position measurement data, the calculated variables describing a correlation between the position signals of the position sensors are correlation coefficients for each degree of freedom of the medical instrument, calculating variables describing a dimension of the divergence of captured and previously measured position measurement data, the calculated variables describing a dimension of the divergence of captured and previously measured position measurement data are variances for each degrees of freedom of the medical instrument, determining the respective movement state of the medical instrument by means of an algorithm for classification comprising comparisons of the calculated variables with predetermined values where the algorithm for classification based on a decision tree comprising decision criteria to be checked, each decision criterium comparing the calculated variables to predefined values, depending on the result of a first decision criterium, at least one further decision criterium is checked and at the end of the decision tree a different threshold value is allocated to each of the determined movement states, and filtering the captured position measurement data on the basis of at least one comparison of the allocated threshold value with a predefined plausibility value to determine if the predefined plausibility value exceeds the allocated threshold value; and displaying an image data set based on the filtered captured position measurement data on a display, the image data set including a graphical depiction of the medical instrument, the graphical depiction being displayed on the display only when the predefined plausibility value does not exceed the allocated threshold value.

15. The system as recited in claim 14 wherein the data processor is configured to present or display an image data set determined by the method.

16. The system as recited in claim 14 wherein the at least two electromagnetic position sensors include at least two position sensors are arranged on the medical instrument, wherein at least a first position sensor is arranged on a distal end and at least a second sensor is arranged on a proximal end of the medical instrument.

17. The system as recited in claim 14 further comprising a field coil to generate a field, the at least two electromagnetic position sensors being configured as electromagnetic position sensors responding to the field.

18. The system as recited in claim 14 further comprising an operating system.

19. The system as recited in claim 18 wherein the operating system is selected from at least one of a group consisting of: at least one Unix system, a Unix derivative, a BSD system, a Windows system and an Apple/Macintosh system.

20. The method as recited in claim 14 wherein the determination of the respective movement state of the medical instrument and/or the algorithm for classification comprises checking at least two of the following criteria:

criterion 1: the correlation coefficient of all degrees of freedom are smaller than an experimentally predetermined value;

criterion 2: the correlation coefficients of two degrees of freedom are negative;

criterion 3: the variances of all degrees of freedom of the last three measurements are smaller than an experimentally predetermined value;

criterion 4: the variances of all degrees of freedom of the last three measurements are smaller than an experimentally predetermined value;

criterion 5: the variances of all degrees of freedom of the last measurements are smaller than an experimentally predetermined value;

criterion 6: the correlation coefficients of exactly two degrees of freedom are smaller than an experimentally predetermined value and the remaining degree of freedom has a correlation coefficient which is smaller than a negative experimentally predetermined value.

21. The method as recited in claim 20 wherein it is determined that the movement state is:

a positioning state when:
criteria 1 and 4 are met;
criterion 1 is not met but criteria 2 and 4 are met; or
criteria 1 and 2 are not met but criteria 3 and 4 are met;

a rotation state when:
criterion 1 is met and criterion 4 is not met;
criterion 1 is not met, criterion 2 is met and criterion 4 is not met; or
criteria 1 and 2 are not met, criterion 3 is met and criterion 4 is not met;

a moving state when:
criteria 1, 2, 3, 5 and 6 are not met; or an interference state when:
criteria 1, 2, 3 are not met and criterion 5 is met; or
criteria 1, 2, 3 and 5 are not met and criterion 6 is met.

22. A computer program product disposed on a non-transitory computer readable media, the product comprising program code configured for executing a method for generating position data of a medical instrument when the computer program is executed on a computer, the method comprising the following steps:

capturing position measurement data of at least two electromagnetic position sensors which are arranged on the medical instrument, the position measurement data indicating a measured position of the medical instrument;

determining a movement state of the medical instrument on the basis of the captured position measurement data, the movement state being defined by how the medical instrument is being moved and a speed the medical instrument is being moved, the movement state being one of a positioning state in the medical instrument is kept still in a position or moved or rotated with a speed lower than a predetermined value, a rotation state in which the medical instrument is swung around its own axis, a moving state in which the medical instrument is moved with a speed higher than a predetermined value, and an interference state in which the measured position of the medical instrument is influenced by another object, the determination comprising;

calculating variables describing a correlation between the position signals of the position sensors on the basis of the captured position measurement data, the calculated variables describing a correlation between the position signals of the position sensors are correlation coefficients for each degree of freedom of the medical instrument, calculating variables describing a dimension of the divergence of captured and previously measured position measurement data, the calculated variables describing a dimension of the divergence of captured and previously measured position measurement data are variances for each degrees of freedom of the medical instrument, determining the respective movement state of the medical instrument by means of an algorithm for classification comprising comparisons of the calculated variables with predetermined values where the algorithm for classification based on a decision tree comprising decision criteria to be checked, each decision criterium comparing the calculated variables to predefined values, depending on the result of a first decision criterium, at least one further decision criterium is checked and at the end of the decision tree a different threshold value is allocated to each of the determined movement states, and filtering the captured position measurement data on the basis of at least one comparison of the allocated threshold value with a predefined plausibility value to determine if the predefined plausibility value exceeds the allocated threshold value; and displaying an image data set based on the filtered captured position measurement data on a display, the image data set including a graphical depiction of the medical instrument, the graphical depiction being displayed on the display only when the predefined plausibility value does not exceed the allocated threshold value.

23. The computer program product with the program code as recited in claim 22 created in the programming language C, C++, C#, Java, Delphi, Ada, Fortran, Cobol or in an interpreter or script language such as JavaScript, Python, Perl, Python, Lua, Ruby or Matlab Script or contains machine instructions or machine codes based hereon.

24. The method as recited in claim 22 wherein the determination of the respective movement state of the medical instrument and/or the algorithm for classification comprises checking at least two of the following criteria:

criterion 1: the correlation coefficient of all degrees of freedom are smaller than an experimentally predetermined value;

criterion 2: the correlation coefficients of two degrees of freedom are negative;

criterion 3: the variances of all degrees of freedom of the last three measurements are smaller than an experimentally predetermined value;

criterion 4: the variances of all degrees of freedom of the last three measurements are smaller than an experimentally predetermined value;

criterion 5: the variances of all degrees of freedom of the last measurements are smaller than an experimentally predetermined value;

criterion 6: the correlation coefficients of exactly two degrees of freedom are smaller than an experimentally predetermined value and the remaining degree of freedom has a correlation coefficient which is smaller than a negative experimentally predetermined value.

25. The method as recited in claim 24 wherein it is determined that the movement state is:

a positioning state when:
  criteria 1 and 4 are met;
  criterion 1 is not met but criteria 2 and 4 are met; or
criteria 1 and 2 are not met but criteria 3 and 4 are met;
a rotation state when:
  criterion 1 is met and criterion 4 is not met;
  criterion 1 is not met, criterion 2 is met and criterion 4 is not met; or
criteria 1 and 2 are not met, criterion 3 is met and criterion 4 is not met;
a moving state when:
criteria 1, 2, 3 5, and 6 are not met; or
an interference state when:
  criteria 1, 2, 3 are not met and criterion 5 is met; or
  criteria 1, 2, 3 and 5 are not met and criterion 6 is met.

* * * * *